United States Patent
Maack

(10) Patent No.: US 8,634,517 B2
(45) Date of Patent: Jan. 21, 2014

(54) PORTABLE X-RAY DETECTOR WITH GRID SENSING UNIT AND X-RAY IMAGING SYSTEM FOR AUTOMATIC EXPOSURE SETTING FOR THE PORTABLE X-RAY DETECTOR

(75) Inventor: Hanns-Ingo Maack, Norderstedt (DE)

(73) Assignee: Koninklijke Philips N.V., Eindhoven (NL)

( * ) Notice: Subject to any disclaimer, the term of this patent is extended or adjusted under 35 U.S.C. 154(b) by 844 days.

(21) Appl. No.: 12/438,367

(22) PCT Filed: Aug. 13, 2007

(86) PCT No.: PCT/IB2007/053200
§ 371 (c)(1),
(2), (4) Date: Feb. 23, 2009

(87) PCT Pub. No.: WO2008/023301
PCT Pub. Date: Feb. 28, 2008

(65) Prior Publication Data
US 2010/0002831 A1      Jan. 7, 2010

(30) Foreign Application Priority Data
Aug. 21, 2006 (EP) .................................. 06119252

(51) Int. Cl.
*G21K 1/00*     (2006.01)

(52) U.S. Cl.
USPC .......................................... 378/154; 378/116

(58) Field of Classification Search
USPC ........................................................ 378/186
See application file for complete search history.

(56) References Cited

U.S. PATENT DOCUMENTS

| | | | |
|---|---|---|---|
| 4,205,233 A | 5/1980 | Craig et al. | |
| 6,501,829 B2 * | 12/2002 | Matsumoto et al. | 378/154 |
| 6,850,597 B2 | 2/2005 | Matsumoto et al. | |
| 2002/0080921 A1 * | 6/2002 | Smith et al. | 378/189 |
| 2004/0096035 A1 * | 5/2004 | Yamazaki et al. | 378/97 |
| 2004/0101107 A1 | 5/2004 | Watanabe | |

FOREIGN PATENT DOCUMENTS

| | | |
|---|---|---|
| EP | 1420618 A2 | 5/2004 |
| JP | 2002186614 A | 7/2002 |
| JP | 2004073356 A | 3/2004 |

* cited by examiner

*Primary Examiner* — Hoon Song

(57) ABSTRACT

It is described a portable X-ray system (200), which has sensing means for detecting whether an anti scatter grid (230) is attached to a portable detector (240) or not. The system is able to automatically change the default exposure settings (265 *a*, 265*b*, 265 *c*, 265 *d*), when a grid (230) is removed or attached to the portable detector (240). Thus, the risk of an under- or an over-exposure of the image will be reduced.

24 Claims, 2 Drawing Sheets

PORTABLE X-RAY DETECTOR WITH GRID SENSING UNIT AND X-RAY IMAGING SYSTEM FOR AUTOMATIC EXPOSURE SETTING FOR THE PORTABLE X-RAY DETECTOR

FIELD OF INVENTION

The present invention relates to the field of X-ray imaging, wherein an object under examination is illuminated by X-radiation and the X-radiation, which has penetrated the object, is detected in order to acquire a two-dimensional image of the object. In particular, the present invention relates to a portable X-ray detection device comprising a two-dimensional X-ray detector unit for detecting the X-radiation having penetrated the object under examination.

The present invention further relates to an X-ray imaging system, in particular a medical X-ray imaging system, the X-ray imaging system comprising the described portable X-ray detector.

Further, the present invention relates to a method for acquiring X-ray image data by means of the described portable detector.

Furthermore, the present invention relates to a computer-readable medium and to a program element having instructions for executing the above-mentioned method for acquiring X-ray image data by means of the described portable detector.

ART BACKGROUND

In medical X-ray imaging patients are X-ray examined either by means of a stationary X-ray imaging system being located typically in special designed X-ray laboratory rooms or by means of a movable X-ray imaging system. Movable X-ray imaging systems are frequently used if a patient is not transportable.

A stationary X-ray imaging system typically comprises a so-called bucky unit. A bucky unit is a box, which comprises a tray for an X-ray cassette, additionally an anti scatter grid and a so-called Automatic Exposure Control (AEC) unit. An anti scatter grid is used for instance for chest exposures in the intensive care department, especially for heavy patients. The grid improves the image quality significantly in particular for thick objects. The anti scatter grid can be optionally removed from the bucky unit. The AEC may be used for controlling an X-ray source in order to allow for optimally exposed images with and without an anti scatter grid.

A movable X-ray imaging system is usually operated by using a free cassette for detecting X-rays, which have traversed a non transportable patient under examination. A free cassette is typically positioned just below the patient.

U.S. Pat. No. 4,205,233 discloses an X-ray radiographic table, which comprises a bucky frame having a front opening through which a bucky unit respectively a bucky tray may be inserted into the frame. The bucky tray supports a cassette, which carries an X-ray sensitive film. The cassette is centered on the bucky tray between adjustable clamps and is adapted to be aligned with an X-ray source.

JP 2004-073356 A discloses radiographic equipment comprising (a) a grid detection means for detecting the presence and absence of the grid, (b) a fixing means for fixing the grid, (c) a fixing detection means for detecting the fixing state of the grid and (d) a posture change restriction means for restricting the operation of the posture change of the photographic equipment. The operation of the posture change restriction means may be controlled according to the detecting result of the grid detection means.

U.S. Pat. No. 6,850,597 B2 discloses an X-ray image photographing apparatus including an X-ray source and an X-ray detector. The X-ray image photographing apparatus further comprises a grid detecting means having a construction for detecting at least (a) the presence or absence of a grid, (b) the kind of the grid and (c) the presence or absence of the replacement of the grid. Further, the X-ray image photographing apparatus comprises an image processing system for image processing and outputting image data collected by the X-ray detector and a memory having stored a plurality of sets of image processing parameters for controlling the image processing system based on an output of the grid detecting means. The image processing starts from selecting a gain image.

EP 1 420 618 A2 discloses an X-ray imaging apparatus including an X-ray source and an X-ray detector on which a plurality of different types of grids are detachably mountable. The X-ray detector includes an automatic exposure control (AEC) unit, which detects the quantity of X-rays emitted from the X-ray generation means and outputs a signal based on the detected quantity. The X-ray imaging apparatus also includes control means controlling the X-ray generation means based on the signal output from the AEC detector, and correcting the AEC detector output according to the type of grid used.

There may be a need for providing X-ray equipment for increasing the reliability of the emitted radiation dose for X-ray imaging in particular for patients being not transportable.

SUMMARY OF THE INVENTION

This need may be met by the subject matter according to the independent claims. Advantageous embodiments of the present invention are described by the dependent claims.

According to a first aspect of the invention there is provided a portable X-ray detection device. The portable X-ray detection device comprises (a) a two-dimensional X-ray detector unit and (b) a sensing unit, which is adapted to recognize whether an anti scatter grid is attached to the X-ray detector unit.

This first aspect of the invention is based on the idea that an automatic sensing of the presence of an optional anti scatter grid provides a reliable and useful information for a radiographer in order to adapt proper default exposure settings of an X-ray source in the moment an anti scatter grid is attached. Therefore, the risk of over- or under-exposures of X-ray images may be reduced. In particular, the risk to apply a too high radiation dose to a patient in case that an anti scatter grid is erroneously not used can be minimized effectively. Therefore, the workflow of acquiring X-ray images is simplified such that also a less experienced user can operate an X-ray imaging system comprising the described portable detector.

In this context it is mentioned that an anti scatter grid may be any channel type X-ray absorption device providing for an X-ray attenuation, which compared to direct X-rays is different for scattered X-rays impinging onto the detector under at least a slightly slanted angle. Therefore, scattered radiation having a different angle of incidence may be suppressed such the contrast of the resulting X-ray images may be increased significantly. This means that the anti scatter grid removes radiation being scattered predominately in thick objects and thus improves the image contrast and the signal to noise ratio. For thin objects an anti scatter grid is typically not used because compared to the effect of a contrast enhancement the effect of deteriorating the signal to noise ratio is too big.

The X-ray detector unit may be any type of X-ray sensitive element such as a radiographic film. However, since modern X-ray imaging systems usually rely on a digital image acquisition the X-ray detector unit might be a digital detector, which comprises an array of X-ray sensor elements. Thereby, each sensor element is capable of receiving an individual radiation dose, wherein the height of an output signal of that sensor element depends or is proportional to the individual radiation dose impinging onto the corresponding sensor element.

Preferably, the portable X-ray detection device comprises a holder or a fixations means, which allows for a precise spatial positioning of an anti scatter grid relative to the X-ray detector unit. A detachably fixation of an anti scatter grid may be realized for instance by means of a clip mechanism, which allows for an easy handling of the anti scatter grid.

According to an embodiment of the invention the portable X-ray detection device comprises a handle, which is adapted to facilitate a manual transportation of the portable X-ray detection device. The provision of a handle has the advantage that the portable X-ray detection device may be transported in an ergonomic advantageous manner to almost any location where an X-ray examination of a non-transportable patient is required.

According to a further embodiment of the invention the portable X-ray detection device has a weight of less than 10 kg, preferably less than 8 kg and more preferably less than 6 kg. By contrast to so-called stationary X-ray detectors, which are used for stationary X-ray imaging systems and which typically have a weight of approximately 20 kg or even more, for the benefit of a comparatively easy transportation a portable X-ray detector comprises less lead shielding.

According to a further embodiment of the invention the portable X-ray detection device has a flat structure with a height of less than 5 cm, preferably less than 3 cm. This may provide the advantage that the portable X-ray detection device may be positioned even within narrow or small regions, which are available close to a patient. For instance the portable X-ray detection device may be positioned directly under a patient's mattress. Therefore, the flat structure of the portable X-ray detection device allows for an X-ray image data acquisition without amending significantly the posture of a patient under examination. As a consequence, the described portable X-ray detection device is useful for a variety of different medical X-ray imaging applications.

According to a further embodiment of the invention the sensing unit is adapted to recognize the type of an anti scatter grid being attached to the X-ray detector unit. The capability of identifying the type of an anti scatter grid may allow for an even more precise adaptation of default exposure settings of an X-ray source.

According to a further embodiment of the invention the portable X-ray detection device further comprises an automatic exposure control unit (AEC), which is adapted to measure the radiation dose impinging onto the X-ray detector unit in real time. This may provide the advantage that the radiation dose can be monitored and, in case a sufficient radiation dose has been received by the X-ray detector unit, an X-ray source generating the X-radiation can be switched of and/or a shutter can be closed such that no more X-rays impinge onto the X-ray detector unit. This may allow for a reliable operation of the X-ray source even if the X-rays are detected by means of a portable and not by means of a stationary detector.

Preferably, the AEC unit comprises an X-radiation dose measurement device such as an ionization chamber.

According to a further embodiment of the invention the portable X-ray detection device is adapted to be inserted into a bucky unit. In this respect a bucky unit may be any box which is adapted to receive an anti scatter grid and an X-ray detection device in a precise spatial orientation with respect to each other. Optionally, a bucky unit may also be configured in order to receive an ACE unit.

A portable X-ray detection device, which may be inserted into a bucky unit, has the advantage that the portable X-ray detection device may also be used for stationary X-ray systems. Therefore, the portable X-ray detection device may be used for a variety of different purposes.

According to a further aspect of the invention there is provided an X-ray imaging system, in particular a medical X-ray imaging system. The X-ray imaging system comprises (a) an X-ray source, which is adapted to generate X-rays penetrating an object under examination, and (b) a portable X-ray detection device as described above, wherein the portable X-ray detection device is adapted to receive X-rays, which have been penetrated the object under examination.

This aspect of the invention is based on the idea that the portable X-ray detection device might be employed in a beneficial manner for X-ray imaging, in particular for medical X-ray imaging. Thereby, the information being provided by the sensing unit with respect to the presence or absence of an anti scatter grid might be used for operating the X-ray source. In particular, when an anti scatter grid is detected, the X-ray source may be operated in such a manner, that an increased radiation dose is emanated from the X-ray source. By contrast thereto, when there is no anti scatter grid placed in front of the two-dimensional X-ray detector unit, the X-ray source may controlled such that only a reduced X-radiation dose is emanated from the X-ray source. This allows for an automatic exposure control such that an object under examination is only subjected to a radiation dose, which is sufficient in order to acquire high contrast X-ray images.

The X-ray source typically is an X-ray tube. However, the provided portable X-ray detection device may also be used in connection with other X-ray sources such as e.g. a synchrotron radiation source providing for a quasi-focused X-radiation.

According to an embodiment of the invention the X-ray imaging system further comprises an X-ray generator device for providing electric energy to the X-ray source, which X-ray generator device is coupled to the sensing unit. This may provide the advantage that the radiation dose an object under examination is exposed to may be effective controlled in such a manner, that the presence or the absence of an anti scatter grid has a strong influence on the electrical control of the X-ray source. Of course, the X-ray generator device may be coupled directly or indirectly to the sensing unit.

According to a further embodiment of the invention the X-ray imaging system further comprises a control unit, which is coupled both to the portable X-ray detection device and to the X-ray generator device. This may provide the advantage that the operation of the X-ray generator device can be controlled by means of an appropriate software, wherein depending on the presence or absence of an anti scatter grid different parameter datasets are used for the operation of the X-ray generator device.

Preferably, a data connection in between the sensing unit of the portable X-ray detection device and the X-ray generator device is provided, which allows for a real time communication. This means that the information regarding the presence or absence of an anti scatter grid is available immediately after the anti scatter grid has been attached to or removed from the two-dimensional X-ray detector unit.

According to a further embodiment of the invention the control unit is adapted to select one of at least two predefined parameter datasets for operating the X-ray generator device, whereby the selection depends on the presence or absence of an anti scatter grid. Such parameter datasets may be for instance so called Automatic Programmed Radiography (APR) parameter datasets, which may be stored in a memory of the control unit. This means that information from sensing an anti scatter grid is used to control the selection of APR-settings, whereby different APR-settings are available for X-ray examination with and without grid.

Preferably, the APR parameter datasets are selected based on an examination code, which may be available in the control unit. Thereby, an examination code non-ambiguously refers to a selected body part of a patient under examination. Therefore, the optimal radiation dose, which depends on both the respective body part of the patient under examination and the presence or absence of an anti scatter grid may be automatically adjusted. Therefore, an over- or an under-exposure of images can be avoided. As a consequence, the reliability of the X-ray imaging system is increased significantly such that the X-ray imaging system may also be operated by a comparatively poor skilled radiographer without increasing the risk for a wrong X-ray exposure.

However, in this respect it has to pointed out that the parameter datasets as well as the examination codes may also be available from a remote computer or a remote memory by means of a network, such as the WorldWideWeb, from which the parameter datasets may be downloaded. Of course, also the examination codes may also by acquired via a computer network.

According to a further embodiment of the invention the predefined parameter dataset is designed to be used both with and without an anti scatter grid by attaching a grid parameter representing the presence or the absence of the grid. This means that a grid correction factor is not included explicitly within the APR parameter sets. The grid correction factor is rather stored outside the APR parameter sets, wherein one parameter of the APR parameter sets refers to the grid correction factor. This may provide the advantage that the total number of parameter datasets can be reduced effectively by a factor of 2. Thereby, an additional grid correction factor is used for adapting the respective APR parameter set on the presence or absence of an anti scatter grid.

The grid correction factor may include two values. For instance a first value may describe a change of the acceleration voltage of the X-ray source by shifting the acceleration voltage by a predetermined voltage difference. Another second value may describe a multiplication factor for the electron beam current with which the X-ray source is operated.

Preferably, the additional grid correction factor reflects a "rule of thumb" for modifying the high voltage and/or the current of X-ray generator device, which is fed to the X-ray source. The "rule of thumb" knowledge of radiographers how to take an X-ray image with and without an anti scatter grid may by stored within a whole list of APR parameter set. The application of the "rule of thumb" may be triggered by an anti scatter grid detection prior to exposure of the X-ray image.

In order to be sure that an over-exposure of a patient under examination can be excluded each predefined parameter dataset contains a programmed reference for selecting an X-ray exposure corresponding the absence of an anti scatter grid. Therefore, only if an anti scatter grid is detected, the radiation dose originating from the X-ray source will be increased. Notably too, selection of the APR data set corresponding to the body part under examination, in combination with grid correction factor to be applied, constitute selection of an active mode of the X-ray source. The X-ray source is operated in the selected mode to deliver the corresponding radiation dose.

In the following there will be described exemplary embodiments of the present invention with reference to a method for acquiring X-ray image data. It has to be pointed out that of course any combination of features relating to different subject matters is also possible.

According to a further aspect of the invention there is provided a method for acquiring X-ray image data, in particular for acquiring medical X-ray imaging data of a patient under examination. The provided method comprises the steps of (a) recording X-ray attenuation data by means of a portable X-ray detection device as described above, (b) determining the presence or the absence of an anti scatter grid in front of the two-dimensional X-ray detector, and (c) operating an X-ray source based on an output signal of the sensing unit indicating the presence or the absence of an anti scatter grid.

This aspect of the invention is based on the idea that a determination of the presence or the absence of an anti scatter grid may automatically trigger a predetermined operating mode of the X-ray source. Thereby, the radiation dose originating form the X-ray source may be automatically adapted in order to compensate for the X-ray attenuation caused by the anti scatter grid. This may allow for a reliable exposure setting such that an erroneously under- and in particular an erroneously over-exposure of a patient under examination can be effectively avoided.

According to an embodiment of the invention the step of operating an X-ray source is further based on an output signal of an automatic exposure control unit, which is associated with X-ray detector unit. As has already been described above such an online monitoring of the radiation dose may provide the advantage that the X-ray exposure of an object under examination may be immediately stopped if a sufficient radiation dose has been received by the X-ray detector unit in order to allow a high quality X-ray image without having the risk of an over-exposure of a patient under examination.

According to a further embodiment of the invention the step of operating an X-ray source comprises selecting one of at least two predefined parameter datasets for operating the X-ray generator device. This may provide the advantage that the described method may be carried out with taking benefit of so called Automatic Programmed Radiography (APR) parameter datasets. Such APR datasets may include pre-programmed values for e.g. the acceleration voltage of an X-ray tube and the electron beam current of an X-ray tube. Of course, the APR datasets may also depend on the body part of a patient under examination.

According to a further aspect of the invention there is provided a computer-readable medium on which there is stored a computer program for acquiring X-ray image data, in particular for acquiring medical X-ray imaging data of a patient under examination. The computer program, when being executed by a control unit, is adapted for performing embodiments of the above-described method for acquiring X-ray image data.

According to a further aspect of the invention there is provided a program element for acquiring X-ray image data, in particular for acquiring medical X-ray imaging data of a patient under examination. The program element, when being executed by a control unit, is adapted for performing embodiments of the above-described method for acquiring X-ray image data.

The computer program element may be implemented as computer readable instruction code in any suitable programming language, such as, for example, JAVA, C++, and may be stored on a computer-readable medium (removable disk, volatile or non-volatile memory, embedded memory/processor, etc.). The instruction code is operable to program a computer or other programmable device to carry out the intended functions. The computer program may be available from a network, such as the WorldWideWeb, from which it may be downloaded.

It has to be noted that embodiments of the invention have been described with reference to different subject matters. In particular, some embodiments have been described with reference to apparatus type claims whereas other embodiments have been described with reference to method type claims. However, a person skilled in the art will gather from the above and the following description that, unless other notified, in addition to any combination of features belonging to one type of subject matter also any combination between features relating to different subject matters, in particular between features of the apparatus type claims and features of the method type claims is considered to be disclosed with this application.

The aspects defined above and further aspects of the present invention are apparent from the examples of embodiment to be described hereinafter and are explained with reference to the examples of embodiment. The invention will be described in more detail hereinafter with reference to examples of embodiment but to which the invention is not limited.

DETAILED DESCRIPTION

Figure 1:
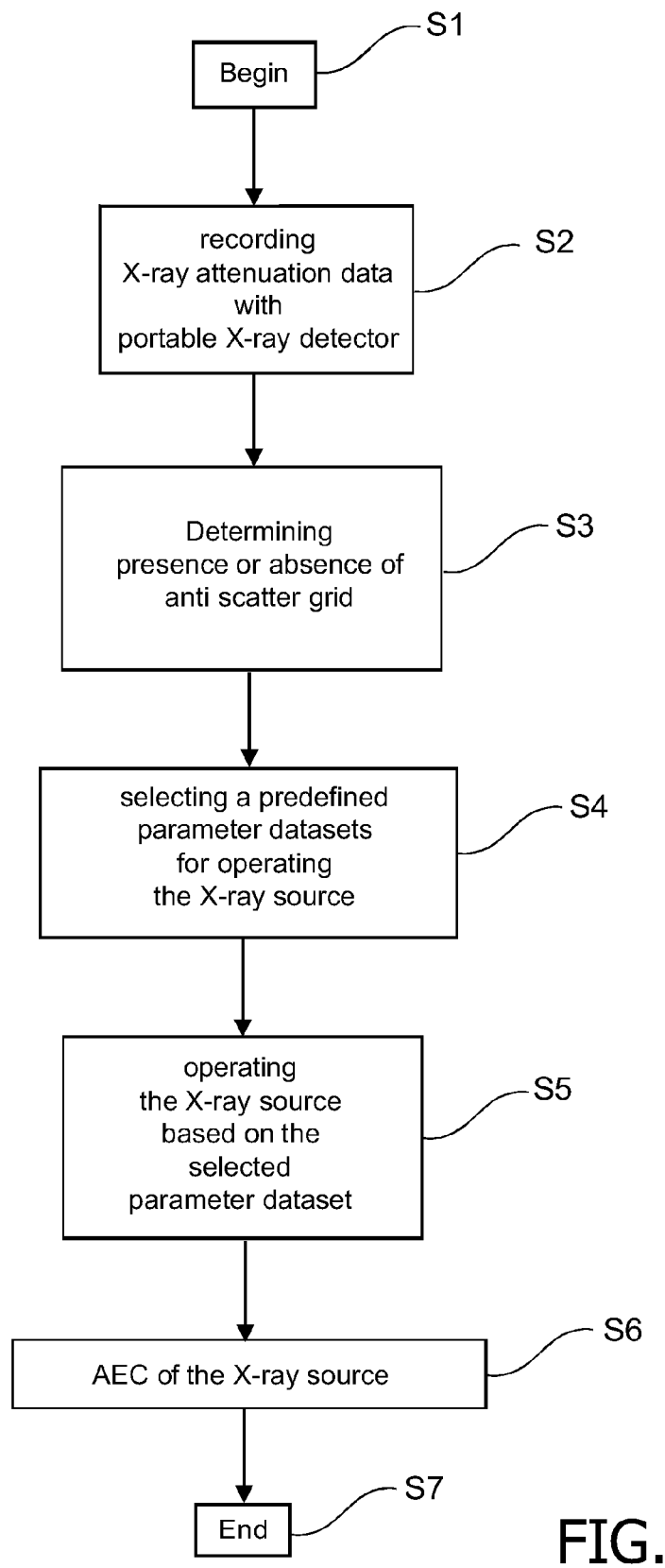
FIG. 1 shows a flow chart on a method for acquiring X-ray image data with a portable X-ray detector according to an embodiment of the invention.

FIG. 1 shows a flow chart how a method for acquiring X-ray image data with a portable X-ray detector may be carried out. The method starts with a step S1.

In step S2 there is recorded a two-dimensional X-ray attenuation data set. Thereby, a portable X-ray detection device is employed, which portable X-ray detection device comprises a two-dimensional X-ray detector unit and a sensing unit, which is adapted to recognize whether an anti scatter grid is attached to the X-ray detector unit.

In step S3 there is determined the presence or the absence of an anti scatter grid in front of the two-dimensional X-ray detector. Thereby, an output signal provided from the sensing unit is evaluated.

In step S4 there is selected a predefined application programmed radiography (APR) parameter dataset from a plurality of different APR parameter datasets, which are stored in a memory associated to a control unit for carrying of the described method for acquiring X-ray image data. The selection depends on the presence or absence of an anti scatter grid. This means that information from sensing an anti scatter grid is used to control the selection of APR-settings, whereby different APR-settings are available for X-ray examination with and without grid.

According to the embodiment described here the APR parameter datasets are selected based on an examination code, which may be available in the control unit. Thereby, an examination code non-ambiguously refers to a defined body part of a patient under examination. Therefore, the optimal radiation dose, which depends on both the respective body part of the patient under examination and the presence or absence of an anti scatter grid may be automatically adjusted.

In step S5 an X-ray tube is operated based on the selected APR dataset. Since the information whether an anti scatter grid is positioned within the X-radiation beam has already been used for selecting an appropriate APR parameter dataset, the X-ray tube is operated under conditions which take into account the presence or absence of an anti scatter grid. The APR parameter dataset in particular includes a first value for the acceleration voltage for electrons impinging onto the anode of the X-ray tube and a second value for the current of the electron beam hitting the anode. Both values have a strong influence on the radiation dose. The first value determines the spectral distribution of the X-radiation wherein the second value determines the intensity of the X-radiation.

In step S6 there is carried out an automatic exposure control of the X-radiation being detected by the X-ray detector unit. Thereby, if an accumulated radiation dose has been reached, which is sufficient for a good quality X-ray image, the X-radiation impinging onto the object under examination is switched off or blocked. This allows for an online monitoring and for an online controlling of the radiation dose a patient is exposed to.

It has to be pointed out that the step S6 is optionally. This means, that the method for acquiring X-ray image data with a portable X-ray detector may be carried out also without this step. However, according to the embodiment described here, carrying out step 6 makes the method more reliable with respect to an erroneous radiation dose.

Figure 2:
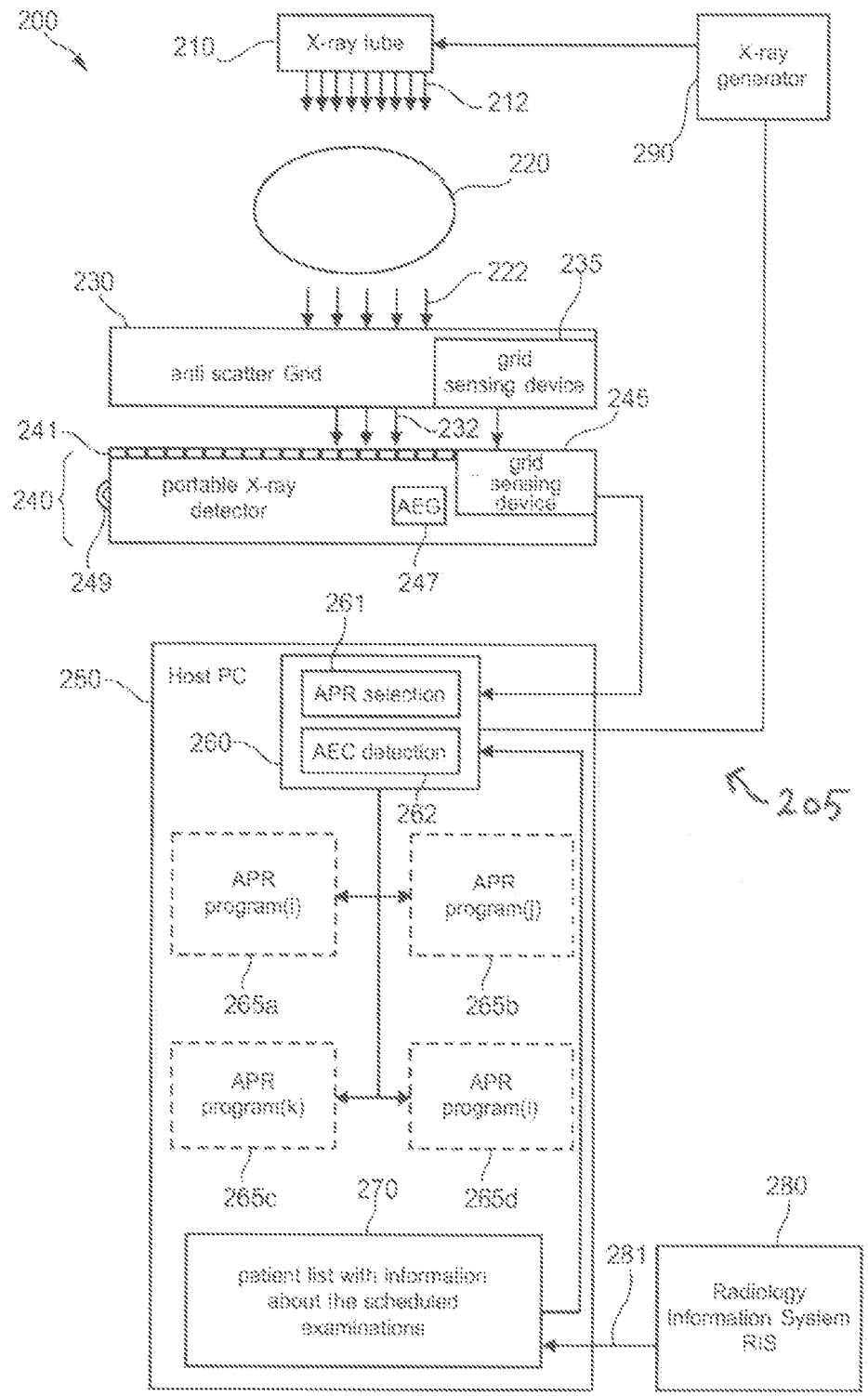
FIG. 2 shows in a schematic representation a block diagram of a medical X-ray imaging system.

FIG. 2 shows in a schematic representation a block diagram of a medical X-ray imaging system 200. The X-ray imaging system 200 comprises an X-ray tube 210, which is adapted to generate X-rays 212 originating from a not depicted anode of the X-ray tube 210. The X-rays 212 penetrate at least partially a patient 220 under examination such that attenuated X-ray 222 impinge onto an anti scatter grid 230, which is fixed directly in front of a portable X-ray detection device 240. The device 240 is operable in connection with a configuration 205, e.g., the rest of FIG. 2 except for the patient 220.

The X-ray tube 210 is controlled respectively driven by an X-ray generator 290 for providing electric energy to the X-ray source 210.

The anti scatter grid 230 may be any channel type X-ray absorption device providing for an X-ray attenuation, which compared to direct X-rays is different for scattered X-rays impinging onto the grid 230 under at least a slightly slanted angle. Therefore, the anti scatter grid 230 removes X-radiation being scattered within nuclei of the patient 220.

Predominately direct X-rays 232, which have not been scattered within the patient 220, penetrate the anti scatter grid 230 and impinge onto a two-dimensional detector array 241 of the portable detector 240. However, independent from the ratio of scattered X-rays the grid 230 definitely reduces the intensity of the X-radiation, which intensity can be detected by the detector array 241. Therefore, according to the embodiment described here, it is ensured that the X-ray intensity being generated by the X-ray source 210 is automatically adapted to the presence or the absence of the anti scatter grid 230.

In order to provide for such an automatic adaptation the portable X-ray detector 240 comprises an active grid sensing device 245. The grid sensing device 245 is capable of detecting an anti scatter grid 230, which is attached in a predefined position in front of the portable X-ray detector 240. The grid detection is realized by means of a passive grid sensing device 235, which is provided at the anti scatter grid 230. The interaction between the passive grid detection device 235 and the active grid sensing device 245 can for instance comprise a mechanical engagement of a nose or any other element projecting from the inner surface of the anti scatter grid 230 into a recess of the active grid sensing device 245. However, the presence of the anti scatter grid 230 can also be detected be closing or opening an electrical contact the passive grid detection device 235 and the active grid sensing device 245. Of course also other interactions such as a magnetic interaction by means of e.g. a reed relay between the passive grid detection device 235 and the active grid sensing device 245 can be used for reliably and effectively sensing the presence of the anti scatter grid 230. Further, the operation of the grid sensing device 245 may also take benefit from a transponder unit and/or any other device using RFID technology. Anyway, according to the embodiment described here, the active grid sensing device 245 generates an output signal, which output signal depends on the presence respectively the absence of the anti scatter grid 230.

In order to effectively avoid an over-exposure of the patient under examination 220 the portable X-ray detector 240 is provided with an automatic exposure control unit 247. The automatic exposure control unit 247 is a measurement device comprising an ionization chamber, which outputs a signal as soon as an accumulated X-ray radiation dose has been reached by means of a single X-ray exposure or a plurality of X-ray exposures. Therefore, the automatic exposure control unit 247 may be useful in order to effectively prevent an erroneously over-exposure of a patient under examination 220.

As can be seen from FIG. 2, the portable X-ray detector 240 is equipped with a handle 249: The handle 249 is adapted to facilitate a manual transportation of the portable X-ray detector 240.

In order to contribute to a comfortable transportation the portable X-ray detector 240 has a weight of less than 8 kg and more preferably less than 6 kg. Therefore, by contrast to so-called stationary X-ray detectors, which are used for stationary X-ray imaging systems and which typically have a weight of approximately 20 kg or even more, the described portable X-ray detector 240 allows for a comparatively easy transportation.

The portable X-ray detector 240 further has a flat structure with a height of less than 5 cm, preferably less than 3 cm. This may provide the advantage that the portable X-ray detector 240 may be positioned for instance directly under a patient's mattress without disturbing significantly the posture of a patient under examination.

The output signal generated by the active grid sensing device 245 is applied to a control unit 250 of the X-ray imaging device 200. The control unit 250 may be realized by means of a host computer such as a PC or a workstation. Further, a stop signal, which may be generated by the automatic exposure control unit 247 is also transferred to the control unit 250.

The control unit 250 comprises, realized either by software, by hardware of by a combination of software and hardware, an application programmed radiography (APR) selection means 261. Since the signal provided by the active grid sensing device 245 includes to information whether a grid is used or not, the APR selection means 261 can select a proper APR parameter dataset from a series of different APR parameter datasets 265a, 265b, 265c and 265d. Each parameter dataset 265a, 265b, 265c or 265d includes values for driving the X-ray source 210 with a predetermined acceleration voltage and a predetermined electron beam current, wherein apart from being adapted to the presence of the anti scatter grid 230 these values are optimized for a specific body part of the patient 220.

The portable detector 240 is adapted to be used both in a so-called "free cassette operation" as well as in a bucky unit of a stationary medical X-ray imaging system. i.e., in either configuration 205. Therefore, according to the embodiment described here, there are four different APR parameter dataset available for controlling the X-ray generator 290 respectively the X-ray tube 220 in order to expose a particular body part of the patient 220 with the proper X-radiation dose.

The first APR parameter dataset (i) is used for an X-ray imaging in the "free cassette operation", wherein neither the anti scatter grid 230 nor the AEC unit 247 is used. This APR parameter dataset (i) is typically used for thin objects like hands or for median thick objects like knees.

The second APR parameter dataset (j) is used for an X-ray imaging in the "free cassette operation", wherein the anti scatter grid 230 is used, but the AEC unit 247 is not used. This APR parameter dataset (i) is typically used for thick objects like abdomen or median thick objects like knees.

The third APR parameter dataset (k) is used for an X-ray imaging, wherein the portable detector 240 is inserted in to a bucky tray of a stationary medical X-ray imaging system. Both the anti scatter grid 230 and the AEC unit 247 are used. This APR parameter dataset (k) is typically used for thick objects like abdomen or chests.

The fourth APR parameter dataset (l) is used for an X-ray imaging, wherein the portable detector 240 is inserted in to a bucky tray. The anti scatter grid 230 is not used whereas the AEC unit 247 is used. This APR parameter dataset (l) is typically used for thin objects under examination.

In order to effectively prevent an over-exposure of the patient 220 the control unit 250 further comprises, realized either by software, by hardware of by a combination of software and hardware, an AEC signal detection means 262, which is coupled to both the AEC unit 247 and the X-ray generator 290. However, it is also possible that the AEC unit 247 is coupled directly to the X-ray generator 290.

The control unit 250 further comprises a memory 270 comprising data representing a patient list with information about the scheduled X-ray imaging examinations. The memory 270 is coupled to the data processor 260 in order to allow for a quick and secure selection of proper APR programs 265a, 265b, 265c and 265d. Thereby, the proper APR program will be selected automatically following an examination code that is available in the memory 270. According to the embodiment described here, the examination code is transferred from a Radiology Information System RIS 280 via a network 281 or a bus system.

Based on the information given with the examination code the radiographer may be able to decide about the use of a grid during the preparation of the X-ray examination. This means that an initially pre-selected APR program will not always match with the current need. If initially the pre-selected APR program (i) has been selected for a "no grid operation" but now a grid has to be used, the APR setting has to be overridden to APR program (j). According to the embodiment described herewith, the proper APR program selection of (i) to (j) can be done automatically by the medical X-ray imaging system 200. Therefore, the probability of generating a proper X-ray radiation dose is increased significantly such that a potential source of error is eliminated, which source of error is existent when APR programs are selected manually.

The APR program may include a so-called grid correction factor, which includes two values. A first value describes a change of the acceleration voltage of the X-ray source by shifting the acceleration voltage by a predetermined voltage difference. A second value describes a multiplication factor for the electron beam current with which the X-ray source is operated. For example, the APR program for a knee may have an acceleration voltage of 60 kV and an electron beam current of 5 mAs when no anti scatter grid is used. Using an anti scatter grid would increase these values by a voltage difference of 3 kV and by a factor of 2. This would lead to an acceleration voltage of 63 kV and an electron beam current of 10 mAs.

Of course, such a rule of thumb can be applied to any APR programs, which do not need to be modified at all. Such rules would be very similar to the rules applied by the radiographer today.

This rule of thumb can be for instance implemented in a program code by the following instructions:

IF grid=yes and APR-default=grid_no THEN increase kV and mAs using delta_kV and mAs-factor IF grid=no and APR-default=grid_yes THEN decrease kV and mAs using delta_kV and mAs-factor.

It should be noted that the term "comprising" does not exclude other elements or steps and the "a" or "an" does not exclude a plurality. Also elements described in association with different embodiments may be combined. It should also be noted that reference signs in the claims should not be construed as limiting the scope of the claims.

In order to recapitulate the above described embodiments of the present invention one can state:

It is described a portable X-ray system 200, which has sensing means for detecting whether an anti scatter grid 230 is attached to a portable detector 240 or not. The system is able to automatically change the default exposure settings 265a, 265b, 265c, 265d, when a grid 230 is removed or attached to the portable detector 240. Thus, the risk of an under- or an over-exposure of the image will be reduced.

List of reference signs:

| | |
|---|---|
| S1 | step 1 |
| S2 | step 2 |
| S3 | step 3 |
| S4 | step 4 |
| S5 | step 5 |
| S6 | step 6 |
| S7 | step 7 |
| 200 | medical X-ray imaging system |
| 205 | configuration |
| 210 | X-ray source/X-ray tube |
| 212 | X-radiation originating from X-ray source |
| 220 | object/patient under examination |
| 222 | X-radiation penetrating patient |
| 230 | anti scatter grid |
| 232 | X-radiation leaving anti scatter grid/X-radiation impinging onto detector |
| 235 | grid sensing device (passive) |
| 240 | portable X-ray detection device/portable X-ray detector |
| 241 | two dimensional X-ray detector unit/detector array |
| 245 | grid sensing device (active) |
| 247 | automatic exposure control unit |
| 249 | handle |
| 250 | control unit/host computer |
| 260 | data processor |
| 261 | APR selection means |
| 262 | AEC signal detection means |
| 265a | first APR program |
| 265b | second APR program |
| 265c | third APR program |
| 265d | fourth APR program |
| 270 | memory |
| 280 | Radiology Information System |

-continued

List of reference signs:

| | |
|---|---|
| 281 | bus system/network |
| 290 | X-ray generator device |

The invention claimed is:

1. A portable X-ray detection device comprising:
a two-dimensional X-ray detector unit; and
a sensing unit configured for recognizing whether an anti scatter grid is attached to said X-ray detector unit,
said portable X-ray detection device being configured for operability in connection, one at a time, with any from among a plurality of configurations for, automatically and without need for user intervention: a) selecting, based on output of said sensing unit indicating a result of said recognizing, an active mode of an X-ray source; and b) operating said source in said mode.

2. A portable X-ray detection device according to claim 1, further comprising:
a handle configured for facilitating a manual transportation of the portable X-ray detection device.

3. A portable X-ray detection device according to claim 1, having a weight of less than 10 kg.

4. A portable X-ray detection device according to claim 1, the portable X-ray detection device having a flat structure with a height of less than 5 cm.

5. A portable X-ray detection device according to claim 1, wherein the sensing unit is configured for recognizing a type of said grid being attached to said X-ray detector unit.

6. A portable X-ray detection device according to claim 1, further comprising:
an automatic exposure control unit configured for measuring a radiation dose impinging onto said X-ray detector unit in real time.

7. A portable X-ray detection device according to claim 1, configured for being inserted into a box that is configured to receive said grid and said device in a predetermined spatial orientation with respect to each other.

8. A medical X-ray imaging system comprising:
a portable X-ray detection device according to claim 1, configured to receive X-rays generated by said X-ray source that have penetrated an object under examination.

9. The system of claim 8, further comprising:
coupled to said sensing unit, an X-ray generator device for providing electric energy to said X-ray source.

10. The system of claim 9, further comprising:
a control unit configured for coupling both to said portable X-ray detection device and to said X-ray generator device.

11. A portable X-ray detection device according to claim 1, configured for transportation, as a portable device, from a current one to a next one of the plural configurations so as to entail removal of said device out of current connection with said current one and insertion of said device into connection with said next one.

12. A portable X-ray detection device according to claim 11, said removal being manual and from a receptacle, said insertion being manual and into a receptacle.

13. A portable X-ray detection device according to claim 11, said current one and said next one differing only as to location.

14. A portable X-ray detection device according to claim 11, said current one and said next one being configured for utilizing output of said sensor unit and of said two-dimensional X-ray detector unit.

15. The portable X-ray detection device of claim 1, configured for, responsive to said grid being attached or removed, real time communication to an X-ray generator device.

16. A portable X-ray detection device according to claim 7, further configured for use in a movable medical X-ray imaging system that does not use automatic exposure control.

17. A portable X-ray detection device according to claim 16, comprising an automatic exposure control unit.

18. A portable X-ray detection device according to claim 3, having a weight less than 6 kg.

19. An X-ray imaging system, in particular a medical X-ray imaging system, the X-ray imaging system comprising:
   an X-ray source, which is adapted to generate X-rays penetrating an object under examination:
   a portable X-ray detection device comprising: a two-dimensional X-ray detector unit and a sensing unit, which is adapted to recognize whether an anti scatter grid is attached to the X-ray detector unit, wherein the portable X-ray detection device is adapted to receive X-rays, which have been penetrated the object under examination;
   an X-ray generator device for providing electric energy to the X-ray source, which X-ray generator device is coupled to the sensing unit; and
   a control unit, which is coupled both to the portable X-ray detection device and to the X-ray generator device, wherein the control unit is adapted to select one of at least two predefined parameter datasets for operating the X-ray generator device, whereby the selection depends on the presence or absence of an anti scatter grid, the predefined parameter datasets being designed to be used both with and without said grid by attaching a grid parameter representing said presence or absence of said grid.

20. A non-transitory computer-readable medium on which there is stored a computer program for acquiring medical X-ray imaging data of a patient under examination, the computer program being configured for, when being executed by a control unit, performing a plurality of acts, the plural acts comprising:
   recording X-ray attenuation data by means of a portable X-ray detection device comprising:
      a two-dimensional X-ray detector unit; and
      a sensing unit configured for recognizing whether an anti scatter grid is attached to said X-ray detector unit; and
   automatically and without need for user intervention: a) selecting, based on output of said sensing unit indicating a result of said recognizing, an active mode of an X-ray source; and b) operating said source in said mode.

21. A medical X-ray imaging system configured for receiving a portable X-ray detection device, said device comprising:
   a two-dimensional X-ray detector unit; and
   a sensing unit configured for recognizing whether an anti scatter grid is attached to said X-ray detector unit,
   said medical X-ray imaging system being configured for, automatically and without need for user intervention: a) selecting, based on output of said sensing unit indicating a result of said recognizing, an active mode of an X-ray source; and b) operating said source in said mode.

22. A method for making a medical X-ray imaging system configured for receiving a portable X-ray detection device, said device comprising:
   an X-ray detector unit; and
   a sensing unit configured for recognizing whether an anti scatter grid is attached to said X-ray detector unit, said portable X-ray detection device being operable in connection, one at a time, with any from among a plurality of configurations,
   said method comprising:
      creating a configuration from among the plural configurations and, in doing so, configuring it for, automatically and without need for user intervention: a) selecting, based on output of said sensing unit indicating a result of said recognizing, an active mode of an X-ray source; and b) operating said source in said mode.

23. The method of claim 22, said selecting being from among a plurality of active modes, an active mode from among the plural active modes being a predetermined operating mode for automatically, in case said grid is attached, adjusting, in compensation for X-ray attenuation caused by said grid, a radiation dose originating from said source.

24. A method for making a portable X-ray detection device, comprising:
   configuring said portable X-ray detection device, comprising a two-dimensional X-ray detector unit and a sensing unit configured for recognizing whether an anti scatter grid is attached to said X-ray detector unit, for operability in connection, one at a time, with any from among a plurality of configurations for, automatically and without need for user intervention: a) selecting, based on output of said sensing unit indicating a result of said recognizing, an active mode of an X-ray source; and b) operating said source in said mode.

* * * * *